US007820385B2

United States Patent
Rajeevan et al.

(10) Patent No.: US 7,820,385 B2
(45) Date of Patent: Oct. 26, 2010

(54) METHOD FOR RETAINING METHYLATION PATTERN IN GLOBALLY AMPLIFIED DNA

(75) Inventors: Mangalathu S. Rajeevan, Lilburn, GA (US); Elizabeth R. Unger, Doraville, GA (US)

(73) Assignee: The United States of America as represented by the Department of Health and Human Services, Centers for Disease Control and Prevention, Washington, DC (US)

(*) Notice: Subject to any disclaimer, the term of this patent is extended or adjusted under 35 U.S.C. 154(b) by 646 days.

(21) Appl. No.: 11/689,423

(22) Filed: Mar. 21, 2007

(65) Prior Publication Data
US 2007/0238117 A1    Oct. 11, 2007

Related U.S. Application Data

(60) Provisional application No. 60/785,000, filed on Mar. 22, 2006.

(51) Int. Cl.
C12Q 1/68    (2006.01)
C12P 19/34    (2006.01)

(52) U.S. Cl. .......................................... 435/6; 435/91.2
(58) Field of Classification Search ........................ None
See application file for complete search history.

(56) References Cited

U.S. PATENT DOCUMENTS

| 6,214,556 | B1 | 4/2001 | Olek et al. |
| 6,265,171 | B1 | 7/2001 | Herman et al. |
| 6,331,393 | B1 | 12/2001 | Laird et al. |
| 6,335,165 | B1 | 1/2002 | Navot et al. |
| 6,617,137 | B2 * | 9/2003 | Dean et al. ................. 435/91.1 |
| 6,884,586 | B2 | 4/2005 | Van Ness et al. |
| 7,288,373 | B2 * | 10/2007 | Millar et al. ................... 435/6 |
| 2003/0032026 | A1 | 2/2003 | Berlin |
| 2003/0082600 | A1 | 5/2003 | Olek et al. |

(Continued)

FOREIGN PATENT DOCUMENTS

WO    WO 01/68910    9/2001

(Continued)

OTHER PUBLICATIONS

Gitan et al. (2002) Genome research vol. 12: pp. 158-164.*

(Continued)

*Primary Examiner*—Kenneth R. Horlick
(74) *Attorney, Agent, or Firm*—Klarquist Sparkman, LLP.

(57) ABSTRACT

A method for preserving information about cytosine methylation status in amplified nucleic acid molecules is disclosed. The method includes contacting a sample that contains nucleic acid molecules, such as nucleic acid molecules having or suspected of having methylated cytosines, with a modifying agent that converts the unmethylated cytosines to produce converted nucleic acid molecules. The converted nucleic acid molecule retains information about cytosine methylation. The method further involves contacting the sample with a DNA polymerase to amplify the converted nucleic acid molecules by multiple strand displacement amplification. The sample is not contacted with a nucleic acid ligase or an RNA polymerase. Also disclosed are methods for detecting cytosine methylation in a sample. Such methods include detecting the presence of the signature of cytosine methylation in a bisulfite treated DNA sample that has been amplified by multiple strand displacement.

32 Claims, 6 Drawing Sheets

U.S. PATENT DOCUMENTS

| | | |
|---|---|---|
| 2003/0119025 A1 | 6/2003 | Olek et al. |
| 2003/0129620 A1 | 7/2003 | Olek et al. |
| 2003/0157510 A1 | 8/2003 | Olek et al. |
| 2004/0152080 A1 | 8/2004 | Berlin |
| 2004/0241704 A1 | 12/2004 | Markert-Hahn et al. |
| 2005/0037393 A1 | 2/2005 | Gunderson et al. |
| 2005/0064428 A1 | 3/2005 | Berlin |
| 2005/0153296 A1 | 7/2005 | Berlin |
| 2005/0153316 A1 | 7/2005 | Jeddeloh et al. |
| 2005/0181394 A1 | 8/2005 | Steemers et al. |

FOREIGN PATENT DOCUMENTS

| | | |
|---|---|---|
| WO | WO 03/000926 | 1/2003 |
| WO | WO 03/002760 | 1/2003 |
| WO | WO 03/085132 | 10/2003 |
| WO | WO 2004/059007 | 7/2004 |

OTHER PUBLICATIONS

Fackler et al., "Quantitative Multiplex Methylation-Specific PCR Assay for the Detection of Promoter Hypermethylation in Multiple Genes in Breast Cancer," *Cancer Research*, 64:4442-4452, 2004.

Galm et al., "Enzymatic Regional Methylation Assay: A Novel Method to Quantify Regional CpG Methylation Density," *Genome Research*, 12:153-157, 2001.

Galm et al., "Methylation-Specfic Polymerase Chain Reaction," *Methods in Molecular Medicine*, 113:279-291.

Herman et al., "Methylation-specific PCR: A novel PCR assay for methylation status of CpG islands," *Proc. Natl. Acad. Sci* 93:9821-9826, 1996.

Lage et al., "Whole Genome Analysis of Genetic Alterations in Small DNA Samples Using Hyperbranched Strand Displacement Amplification and Array-CGH," *Genome Research*, 13:294-307, 2003.

Laird et al., "Hairpin-bisulfite PCR: Accessing epigenetic methylation patterns on complementary strands of individual DNA molecules," *PNAS*, 2004, Abstract.

Lewin et al., "Quantative DNA methylation analysis based on four-dye trace data from direct sequencing of PCR amplificates," *NCBI*, 20(17):3005, 2004, Abstract.

Liu et al., "Polymerase chain reaction-based methods of DNA methylation analysis," *Analytical Biochemistry*, 317:259-265, 2003.

Maekawa et al., "DNA methylation analysis using bisulfite treatment and PCR-single-strand conformation polymorphism in colorectal cancer showing microsatellite instability," *NCBI*, Abstract.

Melnikov et al., "MSRE-PCR for analysis of gene-specific DNA methylation," *Nucleic Acids Research*, 33(10):1-7, 2005.

Mill et al. "Whole genome amplification of sodium bisulfite-treated DNA allows the accurate estimate of methylated cytosine density in limited DNA resources," *BioTechniques*, (41)5:603-607, 2006.

Miner et al., "Molecular barcodes detect redundancy and contamination in hairpin-bisulfite PCR," *Nucleic Acids Research*, 32(17):1-4, 2004.

Olek et al., "A modified and improved method for bisulphite based cytosine methylation analysis,"*Nucleic Acids Research*, 24(24): 5064-5066, 1996.

Warnecke et al., "Detection and measurement of PCR bias in quantitative methylation analysis of bisulphite-treated DNA," *Nucleic Acids Research*, 25(21):4422-4426, 1997.

Worm et al., "In-Tube DNA Methylation Profiling by Fluorescence Melting Curve Analysis," *Clinical Chemistry*, 47(7):1183-1189, 2001.

Yang et al., "A simple method for estimating global DNA methylation using bisulfite PCR of repetitive DNA elements," *Nucleic Acids Research*, 32(3):1-6, 2004.

\* cited by examiner

Primers

Template Strand

Elongation

Strand Displacement

Multiple Strand Displacement

Unamplified Bisulfite Treated DNA

MDA Amplified Bisulfite Treated DNA

METHOD FOR RETAINING METHYLATION PATTERN IN GLOBALLY AMPLIFIED DNA

CROSS REFERENCE TO RELATED APPLICATION

This application claims the benefit of U.S. Provisional Application No. 60/785,000, filed Mar. 22, 2006, which is incorporated by reference herein in its entirety.

FIELD

This disclosure relates to methods of amplifying nucleic acids, wherein the amplified nucleic acids retain information about cytosine methylation status.

BACKGROUND

DNA methyltransferases (also referred to as DNA methylases) transfer methyl groups from the universal methyl donor S-adenosyl methionine to specific sites on a DNA molecule. Several biological functions have been attributed to the methylated bases in DNA, such as the protection of the DNA from digestion by restriction enzymes in prokaryotic cells. In eukaryotic cells, DNA methylation is an epigenetic method of altering DNA that influences gene expression, for example during embryogenesis and cellular differentiation. The most common type of DNA methylation in eukaryotic cells is the methylation of cytosine residues that are 5' neighbors of guanine ("CG" dinucleotides also referred to as "CpGs"). In eukaryotic cells, the methylation of cytosine residues occurs predominantly in CG poor loci (Bird, *Nature* 321:209, 1986). In contrast, discrete regions of CG dinucleotides called CpG islands typically remain unmethylated in normal cells, except during X-chromosome inactivation and parental specific imprinting (Li, et al., *Nature* 366:362, 1993) where methylation of 5' regulatory regions can lead to transcriptional repression (Willson, *Trends Genet.* 7:107-109, 1991). For example, if a site in the promoter of the gene is methylated, gene silencing is likely to occur.

Improper methylation of DNA is believed to be the cause of some diseases such as Beckwith-Wiedemann syndrome and Prader-Willi syndrome (Henry et a., *Nature* 351:665, 1991; Nicholls et al., *Nature* 342:281, 1989). It has also been purposed that improper methylation is a contributing factor in many cancers (Laird and Jaenisch, *Hum. Mo. Genet.* 3 Spec. No.: 1487-1495, 1994). For example, de novo methylation of the Rb gene has been demonstrated in retinoblastomas (Sakai, et al., *Am. J Hum. Genet.* 48:880, 1991). In addition, expression of tumor suppressor genes have been shown to be abolished by de novo DNA methylation of a normally unmethylated 5' CpG island (Issa et al., *Nature Genet.*, 7:536, 1994; Herman et al., *Proc. Natl. Acad. Sci., U.S.A.*, 91:9700, 1994; Merlo et al., *Nature Med.*, 1:686, 1995; Herman et al., *Cancer Res.*, 56:722, 1996; Graff et al., *Cancer Res.*, 55:5195, 1995; Herman et al., *Cancer Res.*, 55:4525, 1995). Many additional effects of methylation are discussed in detail in published International Patent Application PCT/US00/02530.

Current methods used to determine the methylation status of DNA, such as methylation sensitive single nucleotide primer extension (Ms-SNuPE), require a relatively large amount of sample DNA. The amount of DNA in non-invasively collected samples such as blood, urine or shed cells remains the most significant limiting factor in global and targeted methylation studies. In many epigenetic studies, the amount of genomic DNA starting material is limited, especially in experiments utilizing valuable clinical samples, for example oocytes, laser capture microdissected cells, and microscope slides. Current approaches to DNA amplification, such as polymerase chain reaction (PCR) or isothermal whole genome amplification methods, copy the base sequence but do not retain the methylation pattern that was present in the original DNA. Thus, the need exists for methods amplifying DNA while retaining information about the methylation status.

SUMMARY

Methods are disclosed herein for preserving information about cytosine methylation status in amplified nucleic acids. The methods include contacting a sample that contains a nucleic acid molecule with a modifying agent that converts the unmethylated cytosine residues to produce a converted nucleic acid molecule that is subsequently detectable to identify the unmethylated cytosines. Treatment of nucleic acid molecules does not modify methylated cytosine residues and therefore they are not converted by the modifying agent. This difference between the ability of the modifying agent to convert cytosine residues and the inability to convert methylated cytosine residues effectively preserves the information about cytosine methylation status in the converted nucleic acid molecule. In one example, the converted nucleic acid molecule is a nucleic acid molecule in which a modifying agent is bisulfite and the unmethylated cytosine residues are converted to uracil. Alteration in the sequence may then be detected to identify methylated and/or unmethylated cytosine residues in the original sequence. For example, the sequence of a bisulfite treated amplified nucleic acid molecule can be compared to the sequence of an untreated nucleic acid molecule. Methylation status can be determined by examining the differences between these sequences. In one example, the sequence of a bisufite treated amplified nucleic acid is compared to a reference sequence, such as a genomic sequence stored in GENBANK®.

Following treatment with the modifying agent, the sample also is contacted with a DNA polymerase to amplify the converted nucleic acid molecule by multiple strand displacement amplification. During multiple strand displacement amplification of the converted DNA, a cytosine residue is incorporated in positions where an unconverted cytosine residue is present (and guanine is incorporated in the complementary strand), thereby preserving information about cytosine methylation in the amplified nucleic acid sequence. In contrast, at positions where the cytosine was converted a different base is incorporated. In one example, thymidine is incorporated at positions where converted cytosine occurs and adenine is incorporated in the complementary strand. This amplified DNA in which the cytosine methylation status is preserved results from the amplification process. In one example, the DNA polymerase used in the amplification reaction is $\phi 29$ DNA polymerase.

The disclosed methods are surprisingly effective at amplifying DNA in a sample. In addition, the use of this method does not result in the formation of substantially fragmented DNA that is typical of DNA that has been converted with a modifying agent. The disclosed methods do not require the use of a nucleic acid ligase or an RNA polymerase to ligate the fragmented DNA prior to amplification.

In some embodiments, cytosine methylation is determined by detecting unconverted cytosines and/or guanines in a sample of amplified DNA. By exclusion, cytosine methylation can also be deduced by detecting thymidine and/or adenine in the sample of amplified DNA. Thus any method which detects and differentiates between nucleotide bases can be used to deduce the methylation status of the DNA in the sample. In some examples, the nucleotide bases are detected in the amplified nucleic acids using DNA sequencing, polymerase chain reaction (PCR), nucleic acid hybridization, endonuclease digestion, or a combination thereof. In particular embodiments, the nucleotide bases are detected using pyrosequencing. In some embodiments, the nucleotide bases are detected using a microarray, such as a methylation profiling array.

The foregoing and other objects, features, and advantages of the invention will become more apparent from the following detailed description, which proceeds with reference to the accompanying figures.

DETAILED DESCRIPTION

I. Abbreviations

A: Adenine
BST-DNA: Bisulfite treated DNA
C: Cytosine
G: Guanine
MDA: Multiple strand displacement amplification
PCR: Polymerase chain reaction
PNA: Peptide nucleic acid
T: Thymidine
Tm: Melting temperature
TNA: Total nucleic acid
U: Uracil II. Terms Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a primer" includes single or plural primers and can be considered equivalent to the phrase "at least one primer."

As used herein, the term "comprises" means "includes." Thus, "comprising a primer" means "including a primer" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided in the context of the disclosed methods of retaining the methylation pattern in the amplified nucleic acids. These explanations also provide additional description of various techniques for performing the methods.

Animal: A living multi-cellular vertebrate or invertebrate organism, a category that includes, for example, mammals and birds. The term mammal includes both human and non-human mammals. Similarly, the term "subject" includes both human and veterinary subjects.

Amplification: Amplification of a nucleic acid molecule (such as a DNA or RNA molecule) refers to use of a technique that increases the number of copies of a nucleic acid molecule in a sample.

Figure 2:
FIG. 2 is a schematic diagram illustrating multiple strand displacement amplification.
Figure 2:
Figure 2:
Figure 2:

In one example, amplification is multiple strand displacement amplification, such as described in U.S. Pat. No. 6,617,137. A schematic representation of multiple strand displacement amplification is depicted in FIG. 2.

Another example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid molecule. This cycle can be repeated multiple times.

The product of amplification can be characterized by such techniques as electrophoresis, restriction endonuclease cleavage patterns, oligonucleotide hybridization, and/or nucleic acid sequencing.

Other examples of in vitro amplification techniques include quantitative real-time PCR; reverse transcriptase PCR; real-time reverse transcriptase PCR; nested PCR; transcription-free isothermal amplification (see U.S. Pat. No. 6,033,881), repair chain reaction amplification (see PCT publication No. WO 90/01069); ligase chain reaction amplification (see published European Patent No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Archive: A repository, for example a repository of information and/or samples. In one example, an archive is a DNA archive of amplified DNA that contains the methylation signature of DNA from a sample or a plurality of samples.

Bisulfite treatment: The treatment of DNA with bisulfite or a salt thereof, such as sodium bisulfite ($NaHSO_3$). Bisulfite reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by polymerases and amplification will result in an adenine thymine base pair instead of a cytosine guanine base pair.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Contacting: Placement in direct physical association, including both in solid and in liquid form.

Detect: To determine if an agent, such as a particular nucleotide, for example a cytosine, guanine, or methylated cytosine, is present or absent. In some examples, this can further include quantification.

DNA ligase: An enzyme that chemically links two strands of DNA together.

Hybridization: The ability of complementary single-stranded DNA or RNA to form a duplex molecule, which also can be referred to as a hybridization complex. Nucleic acid hybridization techniques can be used to form hybridization complexes between a probe or primer and a nucleic acid molecule, such as hybridization between a primer and a converted nucleic acid molecule.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)

| Hybridization: | 5× SSC at 65° C. for 16 hours |
| Wash twice: | 2× SSC at room temperature (RT) for 15 minutes each |
| Wash twice: | 0.5× SSC at 65° C. for 20 minutes each |

High Stringency (detects sequences that share at least 80% identity)

| Hybridization: | 5×-6× SSC at 65° C.-70° C. for 16-20 hours |
| Wash twice: | 2× SSC at RT for 5-20 minutes each |
| Wash twice: | 1× SSC at 55° C.-70° C. for 30 minutes each |

Low Stringency (detects sequences that share at least 50% identity)

| Hybridization: | 6× SSC at RT to 55° C. for 16-20 hours |
| Wash at least twice: | 2×-3× SSC at RT to 55° C. for 20-30 minutes each. |

Isolated: An "isolated" biological component, such as a nucleic acid molecule, has been substantially separated or purified away from other biological components in which the component naturally occurs, such as other chromosomal and extrachromosomal DNA, RNA, and proteins. Nucleic acid molecules that have been "isolated" include nucleic acid molecules purified by standard purification methods. The term also embraces nucleic acid molecules prepared by recombinant expression in a host cell as well as chemically synthesized nucleic acid molecules, such as probes and primers. Isolated does not require absolute purity, and can include nucleic acid molecules that are at least 50% isolated, such as at least 75%, 80%, 90%, 95%, 98%, 99% or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Methylation: A chemical or biochemical process of introducing a methyl group into an organic molecule. DNA methylation, the addition of a methyl group onto a nucleotide, is a postreplicative covalent modification of DNA that is catalyzed by a DNA methyltransferase enzyme (Koomar et al., Nucl. Acids Res. 22:1-10, 1994; and Bestor et al., J. Mol. Biol. 203:971-983, 1988).

In biological systems, DNA methylation can serve as a mechanism for changing the structure of DNA without altering its coding function or its sequence. DNA methylation is a heritable, reversible and epigenetic change. In some embodiments, it can alter gene expression, particularly by inactivating genes, which has profound developmental and disease consequences. For example, methylation of CpG islands that are associated with tumor suppressor genes can cause decreased gene expression. Increased methylation of such regions can lead to a reduction of normal gene expression, which may cause the selection of a population of cells having a selective growth advantage and thus may become malignant.

Methylation status: The presence or absence of a methylated cytosine, such as a CG dinucleotide in a nucleic acid molecule. Methylation status can be determined directly, for example using a DNA endonuclease that recognizes methylated cytosine. Methylation status can also be determined by exposing a cytosine containing DNA to an agent, such as but not limited to bisulfite, which converts unmethylated cytosine to another nucleotide and determining if the cytosine is resistant to conversion as disclosed herein.

Modifying agent: An agent, such as a chemical agent, that "converts" an unmethylated cytosine to another nucleotide, thereby producing a converted nucleic acid molecule that includes the converted unmethylated cytosine. The modifying agents described herein do not convert methylated cytosine. Thus, converted unmethylated cytosine will distinguish the unmethylated from the methylated cytosine. In some embodiments, the modifying agent converts unmethylated cytosine to uracil. In one example, the modifying agent used for converting unmethylated cytosine is bisulfite or a salt thereof, such as sodium bisulfite ($NaHSO_3$), however, other agents that similarly convert unmethylated cytosine, but not methylated cytosine can also be used.

Not contacted: Not placed in physical association. For example, a sample that as not contacted with an agent, such as a nucleic acid ligase or RNA polymerase, does not have that agent placed in physical association with the sample.

Nuclease: An enzyme capable of cleaving the phosphodiester bond between nucleotides. Nuclease resistant refers to a nucleic acid molecule having at least one bond between nucleotides that cannot be cleaved by a nuclease. Nucleases include both endonucleases and exonucleases. Endonucleases are enzymes that cleave the phosphodiester bond within a polynucleotide chain. Restriction endonucleases (Restriction Enzymes) cleave DNA at specific sites dictated by their recognition sequence. Exonucleases are enzymes that cleave nucleotides one at a time from an end of a polynucleotide chain. These enzymes hydrolyze phosphodiester bonds from either the 3' or 5' terminus of polynucleotide molecules. An "RNAse" is a nuclease that cleaves the phosphodiester bond between ribonucleotides in an RNA strand.

Nucleic acid or nucleic acid molecule: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. Such polynucleotides can be synthesized, for example, using an automated DNA synthesizer.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

A "converted nucleic acid molecule" is a nucleic acid molecule in which on or more of the nucleotides have been chemically converted to another nucleotide, for example with a modifying agent such as bisulfite. In one example, a "converted nucleic acid molecule" is converted such that all of the unmethylated cytosines have been chemically converted to uracil. After amplification, such a converted nucleic acid molecule will have thymine in place of the unmethylated cytosines. The complementary amplified strand will have adenine in place of guanine.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T) and uridine 5'-triphosphate (UTP or U).

Many modified nucleotides (nucleotide analogs) are known and can be used in oligonucleotides, such as the probes and primers for use in the disclosed methods. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl.

Examples of modified base moieties which can be used as modified nucleotides include, but are not limited to: acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, methoxyarninomethyl-2-thiouracil, beta-D-mannosylqueosine, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 3-(3-amino-3-N-2-carboxypropyl) uracil, 2,6-diaminopurine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5'-methoxycarboxymethyluracil, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils, such as 5-methylaminomethyluraci, l5-methyl-2-thiouracil, 5-methoxyuracil, 5-chlorouracil, 5-iodouracil, and cytosines, 7-methylguanine and 7-methyladenine, 8-azaguanine and 8-azaadenine, 7-deazaguanine and 7-deazaadenine, 3-deazaguanine and 3-deazaadenine, amongst others. Additional base modifications can be found for example in U.S. Pat. No. 3,687,808, Englisch et al., *Angewandte Chemie, International Edition*, 1991, 30, 613, and Sanghvi, Chapter 15, Antisense Research and Applications, pages 289-302, Crooke Lebleu ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Nucleotides include those nucleotides containing modified bases, modified sugar moieties and modified phosphate backbones, for example as described in U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,94, herein incorporated by reference to the extent that they describe nucleotide modifications.

Other modified bases are those that function as universal bases. Universal bases include 3-nitropyrrole and 5-nitroindole. Universal bases substitute for the normal bases but have no bias in base pairing. That is, universal bases can base pair with any other base.

Nucleotide analogs can also include modifications of the sugar moiety. Modifications to the sugar moiety would include natural modifications of the ribose and deoxyribose as well as synthetic modifications. Examples of modified sugar moieties which may be used to modify nucleotides at any position on its structure include, but are not limited to: arabinose, 2-fluoroarabinose, xylose, and hexose.

Other modification include those at the 2' position of the sugar: OH; F; O—, S—, or N-alkyl; O—, S—, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[$(CH_2)nO$]m $CH_3$, —O$(CH_2)nOCH_3$, —O$(CH_2)nNH_2$, —O$(CH_2)nCH_3$, —O$(CH_2)n$-$ONH_2$, and —O$(CH_2)nON[(CH_2)nCH_3)]_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, or an intercalator. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. Examples of nucleotides with such modified sugar structures can be found in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference to the extent that that they describe nucleotide modifications.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphoramidothioate, phosphordiamidate, ethylphosphonate, alkyl phosphotriester, boranophosphates, forrmacetal or analogs thereof. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Examples of nucleotides with such modified phosphates and include but are not limited to those found in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference to the extent that they describe nucleotide modifications.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185, 444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference to the extent that they describe nucleotide modifications.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 describe the production and use PNA molecules. (See also Nielsen et al., *Science* 254:1497-1500, 1991).

In one example, a modified nucleotide is a sulfonated cytosine. In one example, a modified nucleotide is a sulfonated uracil.

Polymerizing agent: A compound capable of reacting monomer molecules (such as nucleotides) together in a chemical reaction to form covalently linked linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule according to the disclosed methods include, but are not limited to the *E. coli* DNA polymerase I, specifically the Klenow fragment which has 3' to 5' exonuclease activity (Jacobsen et al., *Eur. J. Biochem.* 45:623-627, 1974), Taq polymerase, reverse transcriptase (such as HIV-1 RT), *E. coli* RNA polymerase, bacteriophage φ29 DNA polymerase (φ29 DNA polymerase is a processive DNA polymerase isolated from the bacteriophage φ29 and is described in for example in U.S.

Pat. Nos. 5,198,543 and 5,001,050), Bst large fragment DNA polymerase (Exo(−) Bst; Aliotta et al., *Genet. Anal. (Netherlands)* 12:185-195, 1996) and exo(−)Bca DNA polymerase (Walker and Linn, *Clinical Chemistry* 42:1604-1608, 1996), phage M2 DNA polymerase (Matsumoto et al., *Gene* 84:247, 1989), phage φ PRD1 DNA polymerase (Jung et al., *Proc. Natl. Acad. Sci. USA* 84:8287, 1987), exo(−)VENT™ DNA polymerase (Kong et al., *J. Biol. Chem.* 268:1965-1975, 1993), T5 DNA polymerase (Chatterjee et al., *Gene* 97:13-19, 1991), SEQUENASE™ (U.S. Biochemicals), PRD1 DNA polymerase (Zhu and Ito, *Biochim. Biophys. Acta.* 1219:267-276, 1994)), and T4 DNA polymerase holoenzyme (Kaboord and Benkovic, *Curr. Biol.* 5:149-157, 1995). A processive DNA polymerases is a DNA polymerase that continuously incorporate nucleotides using the same primer template, without dissociating from either or both the primer or the template molecules, under conditions normally used for primer extension reactions, such as multiple strand displacement amplification. Generally a processive DNA polymerase remains bound to the extended primer or template for at least about 1 kilobase, such as at least about 2 kilobases, at least about 3 kilobases, at least about 4 kilobases, at least about 5 kilobases, at least about 6 kilobases, at least about 7 kilobases, at least about 8 kilobases, at least about 9 kilobases, at least about 10 kilobases or more of extension under suitable conditions. An RNA polymerase is an enzyme that adds ribonucleotides to an elongating chain of RNA.

Primers: Short nucleic acid molecules, such as a DNA oligonucleotide, for example sequences of at least five nucleotides, which can be annealed to a complementary nucleic acid molecule, such as a converted nucleic acid molecule or an amplified converted nucleic acid molecule, such as those described herein, by nucleic acid hybridization to form a hybrid between the primer and the nucleic acid strand. A primer can be extended along the nucleic acid molecule by a polymerase enzyme. Therefore, primers can be used to amplify a nucleic acid molecule, wherein the sequence of the primer is specific for the nucleic acid molecule, for example so that the primer will hybridize to the nucleic acid molecule under high or very high stringency hybridization conditions.

The specificity of a primer increases with its length. Thus, for example, a primer that includes 30 consecutive nucleotides will anneal to a sequence with a higher specificity than a corresponding primer of only 5 nucleotides. Thus, to obtain greater specificity, probes and primers can be selected that include at least 5, at least 6, at least 7, at least 8, at least 9, at least 10, at least 15, at least 20, at least 25, at least 30, at least 35, at least 40, at least 45, at least 50 or more consecutive nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: A probe comprises an isolated nucleic acid molecule capable of hybridizing to a nucleic acid molecule, such as an amplified converted nucleic acid molecule, for example a amplified converted nucleic acid molecule produced by the disclosed methods. A detectable label or reporter molecule can be attached to a probe. Probes can also be attached to a suitable substrate. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base.

Probes for use in the methods disclosed herein are generally at least 15 nucleotides in length, such as at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the nucleic acid molecule, such as 20-60 nucleotides, 20-50 nucleotides, 20-40 nucleotides, or 20-30 nucleotides.

Pyrosequencing: A method of DNA sequencing based chemiluminescent enzymatic reaction, which is triggered when an A, C, G or T is incorporated into the growing DNA chain. Pyrosequencing is described, for example, in U.S. Pat. Nos. 6,210,891 and 6,258,568.

Sample: A sample, such as a biological sample is any sample that includes nucleic acid, in purified or nonpurified form. Samples that can be used with the disclosed methods include any sample obtained from any organism. The specific nucleic acid sequence to be amplified may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human genome.

The nucleic acid-containing sample in which methylation status is to be preserved may be from any source including plant, fungal, bacterial, animal, and viral sources amongst others. The nucleic acid sample can be, for example, a nucleic acid sample from one or more cells, such as prokaryotic or eukaryotic cells, tissue, such as animal or plant tissues, viruses, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy samples, needle aspiration biopsy samples, cancer samples, tumor samples, tissue samples, cell samples, cell lysate samples, crude cell lysate samples, forensic samples, infection samples, and archeological samples such as bone or mummified tissue. If the sample is impure, it may be treated before contact with a modifying agent, such as bisulfite, and multiple strand displacement amplification with an amount of a reagent effective to open the cells, fluids, tissues, or animal cell membranes of the sample. Nucleic acid samples may be extracted by a variety of techniques, for example those described by Maniatis, et al (Molecular Cloning: A Laboratory Manual, Cold Spring Harbor, N.Y., pp 280, 281, 1982).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length, such as 100 consecutive nucleotides or amino acid residues from a sequence set forth in an identified sequence, followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

One indication that two nucleic acid molecules are closely related is that the two molecules hybridize to each other under stringent conditions. Stringent conditions are sequence-dependent and are different under different environmental parameters.

III. Overview of Several Embodiments

Methods are disclosed herein for amplifying methylated DNA, wherein the amplified DNA retains the methylation signature of the template DNA. The methods disclosed herein can be used to create archives of methylated DNA ("Meth-DNA archive"). The creation of such Meth-DNA archives eliminates a significant bottleneck in the collection of methylation information in the genomes of host and pathogens thus providing the opportunity for the early detection, control and prevention of many chronic and infectious diseases of public health importance.

DNA methylation studies have profound significance for both basic and applied research in biology, medicine and agriculture. Deregulation in the methylation of CpG islands may contribute to a variety of cancers, infectious, chronic and neurological diseases. The methods disclosed herein also have universal application in all studies involving any species with in which DNA methylation regulatory mechanisms controls growth, development, and pathogenesis, including eukaryotic organisms such as humans.

One technique for fine mapping of cytosine methylation is the treatment of genomic DNA with sodium bisulfite, which converts unmethylated cytosines to uracils (and subsequently, via amplification, to thymidines), while methylated cytosines are resistant to bisulfite and remain unchanged. After sodium bisulfite treatment, DNA regions of interest are typically amplified and sequenced to identify cytosine to thymidine transitions or stable cytosine positions, respectively corresponding to unmethylated and methylated cytosines in the native DNA. Typically, PCR products are either sequenced directly to provide a strand-specific average sequence for the population of DNA molecules or cloned and sequenced to provide methylation maps of single DNA molecules. Conventional bisulfite treatment has a number of problems resulting from the fact that to ensure the full conversion of unmethylated cytosines, the reaction can result in the large-scale degradation of genomic DNA (Grunau et al. *Nucleic Acids Res.* 29:e65, 2001). Attempts to overcome the problems associated with DNA degradation (such as those described in U.S. patent application Ser. No. 10/871,513) include the concatenation of fragmented DNA by use of a DNA ligase to create concatenated DNA sequences prior to amplification. Because the fragmented DNA can become randomly ligated, the analysis of such ligated sequences can result in the loss of original sequence context, especially in CpG islands. Another method of dealing with the fragmented DNA is to ligate universal priming sites to the ends of the DNA fragments prior to amplification. This method also suffers from a loss of sequence context.

The methods disclosed herein are surprisingly effective at amplifying DNA after treatment with a modifying agent, such as bisulfite. The disclosed methods do not result in significant fragmentation of the DNA, and eliminate the need to treat the sample with a nucleic acid ligase or an RNA polymerase. In addition, methods disclosed herein do not require ligation of the DNA, such as concatenation of the DNA or the addition of priming sites to the ends of the DNA fragments. In certain embodiments, the methods are carried out without one or more of fragmentation of the DNA, treatment with a nucleic acid ligase or RNA polymerase, or ligation of the DNA.

Conversion and Amplification of DNA

Methods are disclosed herein for preserving information about cytosine methylation status in amplified nucleic acid molecules. The methods include contacting a sample that contains nucleic acid molecules, such as nucleic acid molecules having or suspected of having methylated cytosines, with a modifying agent that converts the unmethylated cytosines to produce converted nucleic acid molecules. The methylated cytosines are not converted by the modifying agent. This difference between the converted cytosine and methylated cytosine preserves the information about cytosine methylation status in the converted nucleic acid molecules.

In some embodiments, the modifying agent converts unmethylated cytosine residues to produce uracil. In one specific non-limiting example, the modifying agent is bisulfite. The converted nucleic acid molecules retain the methylation signature of the untreated non-amplified nucleic acid molecules and thus provide information about cytosine methylation status. Reaction of DNA with a modifying agent, such as bisulfite, leads to a conversion of cytosine bases to uracil in two steps after alkaline hydrolysis (Shapiro et al., *Nature* 227, 1047, 1970) resulting in converted nucleic acid molecules. 5-Methylcytosine (methylated cytosine) remains unchanged under these conditions. The conversion of C to U leads to a change in the nucleotide sequence, from which the original 5-methylcytosines can be determined, for example by sequencing, such as by PYROSEQUENCING™.

Cytosine reacts with bisulfite to form a sulfonated cytosine reaction intermediate prone to deamination. This results in the production of sulfonated uracil which can be desulfonated under alkaline conditions to uracil. It is common knowledge that uracil has the base pairing of thymine, which is distinct from cytosine. 5-methylcytosine, which remains unconverted, has the base pairing behavior of cytosine. It is difference in base pairing properties that makes the discrimination of methylated or non-methylated cytosines possible. For example, during amplification a thymine/adenine base pair will be incorporated in place of an unmethylated cytosine/guanine base pair. Kits for performing bisulfite treatments are commercially available, for example as marketed under the trade names CPGENOME™ DNA modification kit (Millipore Corporation, Mass.) and EZ DNA METHYLATION KIT™ (Zymo Research, CA). In some embodiments, the modifying agent is bisulfite or a salt thereof, such as sodium bisulfite ($NaHSO_3$).

The converted nucleic acid molecules are then amplified. The methods further involve contacting the sample with a DNA polymerase to amplify the converted nucleic acid molecules by multiple strand displacement amplification. The DNA polymerase can be a processive DNA polymerase, such as $\phi 29$ DNA polymerase. During multiple strand displacement amplification of the converted DNA, cytosine is incorporated in positions where unconverted cytosine is present thereby preserving information about cytosine methylation in the nucleic acid sequence. Guanine is incorporated at these positions in the complementary strand. In contrast, at positions where the cytosine was converted a different base is incorporated. In one example, thymidine is incorporated at positions where converted cytosine occurred and adenine is incorporated at these positions in the complementary strand. The result of this amplification is an amplified DNA in which the cytosine methylation status is preserved. Specifically, positions that had a methylated cytosine will have cytosine or guanine incorporated in the amplified DNA depending on the orientation of the DNA strand. Conversely, positions that had an unmethylated cytosine will have a thymidine or adenine incorporated depending on the orientation of the DNA strand.

Figure 1:
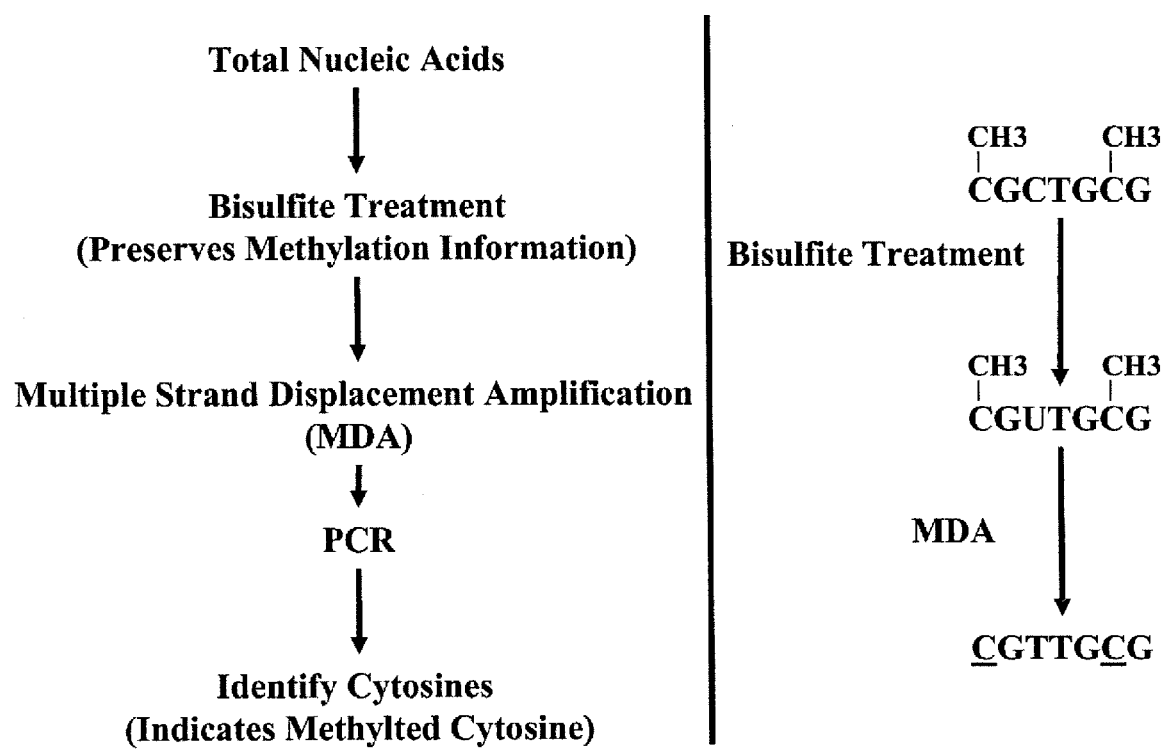
FIG. 1 is a schematic diagram of an exemplary protocol that includes bisulfite treatment and multiple strand displacement.

A nucleic acid ligase or an RNA polymerase is not added to the sample prior to or concomitant with amplification. In one example, the amplification reaction does not include detectable amounts of nucleic acid ligase or RNA polymerase. Furthermore, universal priming sites are not attached to the converted nucleic acid molecules by any method prior to or concomitant with amplification nor is the DNA concatenated prior to or concomitant with amplification. An exemplary schematic representation of an exemplary method encompassed by the present disclosure is depicted in FIG. 1.

In some embodiments, the methods for preserving information about cytosine methylation status in amplified nucleic acid molecules consists of the steps of contacting a sample that contains nucleic acid molecules with a modifying agent that converts the unmethylated cytosines to produce converted nucleic acid molecules. The sample containing the converted nucleic acid molecules is contacted with primers capable of hybridizing to the converted nucleic acid molecules and a DNA polymerase to amplify the converted nucleic acid molecules by multiple strand displacement.

The disclosed methods are applicable to any sample containing DNA for which information about the methylation status is desired. For example, any sample containing nucleic acid, in purified or nonpurified form, can be utilized as the starting nucleic acid or acids, provided it contains, or is suspected of containing a nucleic acid sequence containing methylated cytosines. A sample includes any sample obtained from an organism. Thus, the methods disclosed herein have application to a sample containing nucleic acid molecules from any source, for example a plant, fungal, bacterial, animal, or viral source amongst others. The nucleic acid sample can be, for example, a nucleic acid sample from one or more cells, such as prokaryotic or eukaryotic cells, tissue, such as animal or plant tissues, viruses, or bodily fluids such as blood or blood-fractions, for example, serum or lymphocytes, sputum, saliva, oral washings, skin scrapes, cerebrospinal fluid, prostate fluid, urine, semen, lymphatic fluid, or amniotic fluid, or other biological samples, such as tissue culture cells, buccal swabs, mouthwash, stool, tissues slices, biopsy samples, needle aspiration biopsy samples, cancer samples, tumor samples, tissue samples, cell samples, cell lysate samples, crude cell lysate samples, forensic samples, infection samples, and archeological samples such as bone or mummified tissue. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al, *NEJM* 318:589-93 (1988); and Ognibene et al., *Am. Rev. Respir. Dis.* 129: 929-32 (1984).

If the extracted sample is impure, it may be treated before bisulfite treatment and multiple strand displacement amplification with an amount of a reagent effective to open the cells, fluids, tissues, or animal cell membranes of the sample. Nucleic acid samples may be extracted by a variety of techniques, for example those described by Maniatis, et al. (Molecular Cloning: A Laboratory Manual, Cold Spring Harbor, N.Y., pp 280, 281, 1982), such as alkaline lysis, cesium chloride-gradient purification and the like. Nucleic acid extraction can also be accomplished using a commercially available kit, for example the INSTAGENE™ Matrix, BioRad, Hercules, Calif.; the NucliSens isolation kit, Organon Teknika, Netherlands; the QIAGEN® Tissue Kit, QIAGEN®, Inc., Valencia, Calif.; the MASTERPURE™ extraction kit, Epicentre Technologies, WI and the like.

The need for only small amounts of DNA template in the disclosed method means that the method is useful for DNA amplification from very small samples. In particular, the disclosed method may be used to amplify DNA from a single cell. The ability to obtain analyzable amounts of nucleic acid from a single cell, or similarly small sample, has many applications in preparative, analytical, and diagnostic procedures. Examples of biological samples containing only small amounts of DNA for which amplification by the disclosed method would be useful are material excised from tumors or other archived medical samples, needle aspiration biopsies, clinical samples arising from infections, such as nosocomial infections, forensic samples, embryonic stem cells, embryos, or museum specimens of extinct species.

More broadly, the disclosed method is useful for applications in which the amounts of DNA needed for analysis are greater than the amount in the sample prior to amplification. For example, procedures that analyze DNA by chip hybridization techniques are limited by the amounts of DNA that can be purified. As a result many chip hybridization procedures utilize PCR to generate a sufficient supply of material for the high-throughput procedures; however the use of PCR results in a loss of information about the methylation state of the template DNA. The disclosed method provides for the generation of plentiful amounts of amplified DNA that retains the methylation signature of the starting material.

The DNA sequence, which is the object of amplification, can be any nucleic acid molecule. The sequence can include multiple nucleic acid molecules, such as in the case of whole genome amplification, multiple sites in a nucleic acid molecule, or a single region of a nucleic acid molecule. For multiple strand displacement amplification, generally the sequence is a single region in a nucleic acid molecule or nucleic acid sample. For multiple strand displacement amplification of an entire genome, for example a viral genome, the sequence is the entire genome or nucleic acid sample.

Multiple Strand Displacement Amplification

In the methods disclosed herein, the converted DNA is amplified by multiple strand displacement amplification. DNA polymerases useful in multiple displacement amplification are capable of displacing, either alone or in combination with a compatible strand displacement factor, a hybridized strand encountered during replication. Such polymerases are referred to as strand displacement DNA polymerases. Strand displacement results in the synthesis of multiple copies of a target sequence. The suitability of a DNA polymerase for use in the disclosed methods can be readily determined by assessing its ability to carry out strand displacement replication. In these methods, 5' to 3' exonuclease activity, if present, might result in the destruction of a synthesized strand. In some examples, a strand displacement DNA polymerase lacks 5' to 3' exonuclease activity. In some examples, the DNA polymerases of use are highly processive. Examples of strand displacement DNA polymerases are bacteriophage φ29 DNA polymerase (U.S. Pat. Nos. 5,198,543 and 5,001,050), Bst large fragment DNA polymerase (Exo(−) Bst; Aliotta et al., *Genet. Anal.* (Netherlands) 12:185-195, 1996) and exo(−)Bca DNA polymerase (Walker and Linn, *Clinical Chemistry* 42:1604-1608, 1996). Other useful polymerases include phage M2 DNA polymerase (Matsumoto et al., *Gene* 84:247, 1989), phage φ PRD1 DNA polymerase (Jung et al., *Proc. Natl. Acad. Sci. USA* 84:8287, 1987), exo(−)VENT™ DNA polymerase (Kong et al., *J. Biol. Chem.* 268:1965-1975, 1993), Klenow fragment of DNA polymerase I (Jacobsen et al., *Eur. J. Biochem.* 45:623-627, 1974), T5 DNA polymerase (Chatterjee et al., *Gene* 97:13-19, 1991)), SEQUENASE™ (U.S. Biochemicals), PRD1 DNA polymerase (Zhu and Ito, *Biochim. Biophys. Acta.* 1219:267-276, 1994), and T4 DNA polymerase holoenzyme (Kaboord and Benkovic, *Curr. Biol.* 5:149-157, 1995). In one example, the DNA polymerase is φ29 DNA polymerase Strand displacement can be facilitated through the use of a strand displacement factor, such as helicase. It is considered that any DNA polymerase that can perform strand displacement replication in the presence of a strand displacement factor, is suitable for use even if the DNA polymerase does not perform strand displacement replication in the absence of a strand displacement factor. Strand displacement factors that can be used in strand multiple strand displacement amplification include BMRF1 polymerase accessory subunit (Tsurumi et al., *J. Virology* 67(12):7648-7653, 1993), adenovirus DNA-binding protein (Zijderveld and van der Vliet, *J. Virology* 68(2):1158-1164, 1994), herpes simplex viral protein ICP8 (Boehmer and Lehman, *J. Virology* 67(2):711-715, 1993; Skaliter and Lehman, *Proc. Natl. Acad. Sci. USA* 91(22): 10665-10669, 1994), single-stranded DNA binding proteins (Rigler and Romano, *J. Biol. Chem.* 270:8910-8919, 1995), phage T4 gene 32 protein (Villemain and Giedroc, *Biochemistry* 35:14395-14404, 1996); and calf thymus helicase (Siegel et al., *J. Biol. Chem.* 267:13629-13635, 1992).

In some embodiments, the sample is further contacted with primers capable of hybridizing to the converted nucleic acid molecules. Primers for use in the disclosed amplification method are oligonucleotides that have sequence complementary to the converted nucleic acid molecule which is to be amplified. This sequence is referred to as the complementary portion of the primer. The complementary portion of a primer can be any length that supports specific and stable hybridization between the primer and the target sequence under the reaction conditions, for example conditions of high stringency or very high stringency. Primers for use in the disclosed methods are generally between about 5 to about 60 nucleotides in length, such as about 5 to about 50, about 5 to about 40, about 5 to about 30, about 5 to about 20 nucleotides in length, although longer primers can be used. For example, primers can be about 5 or more nucleotides in length, such as about 5, about 6, about 7, about 8, about 9, about 10, about 11, about 12, about 13, about 14, about 15, about 16, about 17, about 18, about 19, about 20, about 11, about 12, about 13, about 14, about 15, about 16, about 17, about 18, about 19, about 20, about 21, about 22, about 23, about 24, about 25, about 26, about 27, about 28, about 29, about 30, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, or more nucleotides in length.

In some embodiments, the primers have a random nucleotide sequence, such as those using primers of random or degenerate sequence. Thus a collection of primers can be used with a variety of sequences. In such cases, the primers need only be effective in priming nucleic acid synthesis. For example, in whole genome amplification specificity of priming is not essential since the goal generally is to amplify all sequences equally. In some embodiments, the primers are six nucleotides long (hexamers), for example, random hexamer primers where every possible six nucleotide sequence is represented in the set of primers. Short six nucleotide primers can prime multiple strand displacement amplification efficiently. Such short primers are easier to produce as a complete set of primers of random sequence than longer primers at least because there are fewer to make.

Similarly, sets of random primers of other particular lengths, or of a mixture of lengths preferably contain every possible sequence the length of the primer, or, in particular, the length of the complementary portion of the primer can be used. Use of random primers is described in U.S. Pat. Nos. 5,043,272 and 6,214,587.

In some embodiments, the primers are DNA nuclease resistant, for example by the incorporation of modified nucleotide. In some embodiments, the primers contain at least one modified nucleotide such that the melting temperature of the primer is altered relative to a primer of the same sequence without the modified nucleotide(s). Some forms of modified primers, such as RNA/2'-O-methyl RNA chimeric primers, have a higher melting temperature (Tm) than DNA primers. This increases the stability of primer hybridization and will increase strand invasion by the primers, which will lead to more efficient priming. Primers that are composed of ribonucleic acids are DNA exonuclease resistant.

Chimeric primers can also be used. Chimeric primers have at least two types of nucleotides, such as both deoxyribonucleotides and ribonucleotides, both ribonucleotides and modified nucleotides, or that include two or more different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. The DNA and RNA portions of such primers can have random or degenerate sequences. Other forms of chimeric primers are, for example, 5'-(2'-O-Methyl)RNA-RNA-3' or 5'-(2'-O-Methyl)RNA-DNA-3'.

In several embodiments the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides.

In some embodiments, RNA present in the sample can be used as primers for multiple strand displacement amplification. RNA primers are particularly useful for whole genome multiple strand displacement amplification of nucleic acid molecules obtained from biological samples, such as cells or tissue. Since the biological samples contain endogenous RNA, this RNA can be degraded with RNAse to generate a pool of random oligomers, which can then be used to prime the polymerase for amplification of the DNA. This eliminates any need to add primers to the reaction. In some embodiments, the sample is contacted with an RNAse, to producing RNA fragments capable of hybridizing under very high stringency conditions to and directing the amplification of the converted nucleic acid molecules.

Detection of Cytosine Methylation in Amplified DNA

The present disclosure also relates to methods for detecting cytosine methylation in a sample. The methylated cytosine guanine base pair is maintained in the converted amplified nucleic acid molecules. Any method for the detection of cytosine and/or guanine can be used to detect cytosine methylation. Conversely, because conversion and amplification of unmethylated cytosines leads to incorporation of a thymine/adenine base pair, by exclusion, any method for the detection of thymine and/or adenine can be used to detecting cytosine methylation. Methods that detect nucleotide bases and can discriminate between nucleotide bases can be used to detect cytosine methylation in a sample. In several non-limiting examples, the presence of cytosine, guanine, adenine and/or thymine in the amplified DNA can be determined using DNA sequencing, polymerase chain reaction (PCR), nucleic acid hybridization, endonuclease digestion, or a combination thereof. In some embodiments, detecting methylated cytosine in the sample includes determining the nucleic acid sequence of a portion of the amplified nucleic acid molecule and comparing this sequence to a control, wherein a difference between the sequence of the portion of the amplified nucleic acid molecule and the control detects methylated cytosine in the sample. In some examples, a control can be a known DNA sequence corresponding to the nucleic acid sequence of a portion of the amplified nucleic acid molecule for example a reference sequence obtained from GENBANK®. In other examples, a control can be a DNA sequence of a nucleic acid molecule that has not been contacted with the modifying agent that corresponds to the sequence of the portion of the amplified nucleic acid molecule DNA sequencing is well known in the art and is a standard method used to determine the nucleotide sequence of a portion of DNA, such as DNA that has been treated with bisulfite and amplified by multiple strand displacement. DNA sequencing reveals the sequence of DNA and thus can by used to detect the presence of cytosine, guanine, adenine and/or thymine in the DNA, and even the location of cytosine, guanine, adenine and/or thymine within a DNA strand. In some embodiments, cytosine, guanine, adenine and/or thymine are detected by DNA sequencing. In one embodiment, DNA sequencing is PYROSEQUENCING®. PYROSEQUENCING® is well know in the art and a detailed descriptions of PYROSEQUENCING® can be found in U.S. Pat. Nos. 6,210,891 and 6,258,568, which are incorporated herein by reference to the extent they describe PYROSEQUENCING®.

Digestion of the amplified bisulfite treated DNA with an endonuclease can also be used to determine the presence of cytosine, guanine, adenine and/or thymine. By way of example, the amplified nucleic acid molecules only contain cytosine and/or guanine at the positions that were methylated in the sample DNA. Therefore, an endonuclease that requires a cytosine and/or guanine in its recognition sequence will only cut DNA with a cytosine, or guanine, in close proximity to the cut site. For example, many endonucleases recognize about six to about ten base pair regions of DNA. If such an endonuclease requiring a cytosine and/or guanine in its recognition sequence is able to cut amplified bisulfite treated DNA then it follows that a methylated cytosine was present in sample DNA in the region of about six to about ten base pairs recognized by the endonuclease. One of ordinary skill in the art will readily recognize that the choice of nuclease is based on the sequence which information about the methylation status is desired, for example a specific CpG dinucleotide in promoter region. Endonucleases are well known in the art and sufficient guidance on their recognition sequences and their use can be found for example in Maniatis, et al. (Molecular Cloning: A Laboratory Manual, Cold Spring Harbor, N.Y. 1982). After nuclease digestion, the digestion products can be analyzed by any suitable technique, such as PCR, DNA sequencing and the like.

Nucleic acid hybridization techniques can be used to detect the presence of cytosine in a bisulfite treated DNA sample that has been amplified by multiple strand displacement. Several non-limiting examples of hybridization techniques are PCR, the use of methylation profiling arrays, and nucleic acid blotting, such as Southern blotting or dot blotting.

The detection of the presence of cytosine, guanine, adenine and/or thymine can be performed by PCR, for example using sequence specific PCR. PCR primers can be designed that uniquely anneal with converted and amplified DNA that was either methylated or unmethylated prior to conversion and amplification. By way of example, primers can be designed such that they are only capable of hybridizing to the amplified converted DNA if the DNA contains a cytosine, or guanine in the complementary strand, in a particular sequence context. In this example, the presence of a PCR amplification product would indicate that a methylated cytosine was present in the sample DNA. However, the presence of an adenine or thymine in that particular sequence would indicate that an unmethylated cytosine was present in the sample DNA. This technique is typically referred to as "methylation specific PCR (MSP)." In another example, primers can be designed such that they are only capable of hybridizing to the amplified converted DNA if the DNA contains a thymidine, or adenine in the complementary strand, in a particular sequence context. In this example, the presence of a PCR amplification product would indicate that an unmethylated cytosine was present in the sample DNA. However, the presence of a cytosine, or guanine in that particular sequence would indicate that a methylated cytosine was present in the sample DNA.

In another example, PCR primers can be designed to amplify a particular region of DNA. In this way, the PCR primers can amplify the sequence in between the two primers, regardless of the DNA methylation status of that sequence in the original sample DNA. This results in a pool of different PCR products, all with the same length and differing in their sequence only at the sites of potential DNA methylation at cytosines located between the two primers. The presence of cytosine, guanine, adenine, and/or thymine at these positions can then be determined with standard techniques such as DNA sequencing or endonuclease digestion.

Methylation Profiling Arrays

The detection of the presence of a particular base can be performed using nucleic acid arrays, such as methylation profiling arrays. For example, an unmethylated allele of a given DNA sequence is expected to have thymine in place of unmethylated cytosine after treatment with a modifying agent and amplification. Similarly, adenine would be in place of guanine in the complementary strand. Conversely, these sequences remain unchanged in a methylated allele. Converted amplified DNA can be hybridized to arrayed oligonucleotide probes specifically designed to discriminate between converted and unconverted nucleotides (or their complement) at sites of interest.

Figure 6:
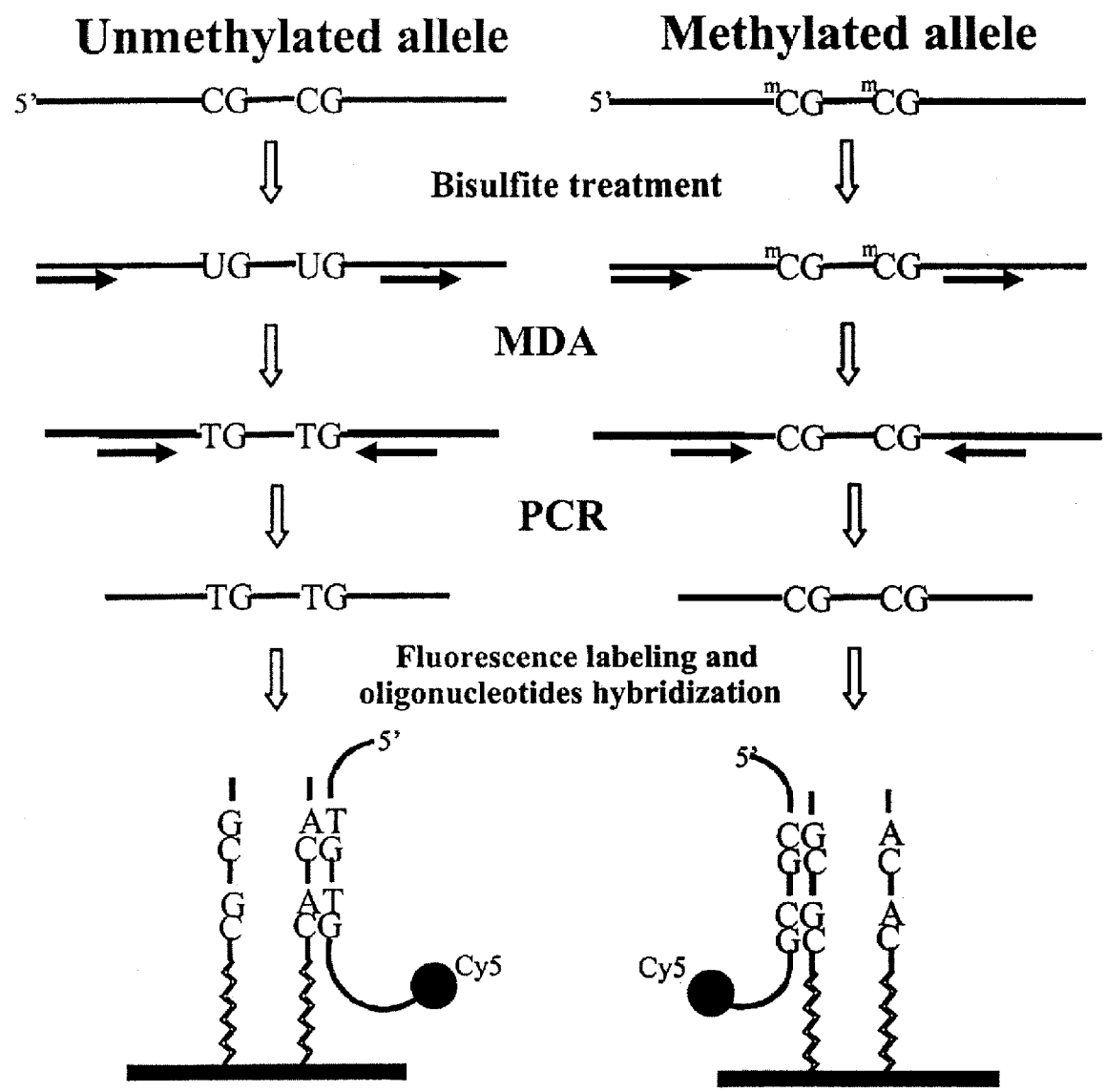
FIG. 6 is a schematic diagram of an exemplary method for analysis of DNA methylation based on an oligonucleotide microarray.

In one embodiment, the presence of particular base is determined with the use of a microarray, such as a methylation profiling array. An exemplary procedure for using methylation profiling arrays is depicted in FIG. 6. With reference to FIG. 6, DNA is bisulfite treated, amplified by multiple strand displacement, and amplified by PCR for a specific region of interest. The amplified product is labeled with Cy5 fluorescent dye and hybridized to oligonucleotide probes attached to a substrate. FIG. 6 left, an oligonucleotide probe is designed to form a perfect match with a target DNA containing the unmethylated allele. FIG. 6 right, a probe is designed to form a perfect match with the methylated DNA target. Thus, a microarray, such as a methylation profiling array, can be used to determine the methylation status of a particular cytosine.

Arrays are arrangements of addressable locations on a substrate, with each address containing a nucleic acid molecule, such as a probe. In some embodiments, each address corresponds to a single type or class of nucleic acid, such as a single probe, though a particular nucleic acid molecule may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, a methylation profiling array is a collection of separate probes at the array addresses. The methylation profiling array is then contacted with a sample of bisulfite treated and amplified nucleic acid molecules for which information about the methylation status of the untreated and unamplified DNA is desired under conditions allowing hybridization between the probe and nucleic acid molecules in the sample to occur. A hybridization signal from an individual address on the array indicates that the probe hybridizes to a nucleotide within the sample. This system permits the simultaneous analysis of a sample by plural probes and yields information the methylation status of nucleic acid molecules contained within the sample. In alternative embodiments, the array contains bisulfite treated and amplified nucleic acid molecule and the array is contacted with a sample containing a probe. In any such embodiment, either the probe or bisulfite treated and amplified nucleic acid molecule may be labeled to facilitate detection of hybridization.

The nucleic acid molecules may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times to provide an added feature to the array, such as redundant activity or to provide internal controls.

Within an array, each arrayed nucleic acid molecule is addressable, such that its location may be reliably and consistently determined within the at least the two dimensions of the array surface. Thus, ordered arrays allow assignment of the location of each nucleic acid molecule at the time it is placed within the array. Usually, an array map or key is provided to correlate each address with the appropriate nucleic acid molecule. Ordered arrays are often arranged in a symmetrical grid pattern, but nucleic acid molecules could be arranged in other patterns, for example, in radially distributed lines, a "spokes and wheel" pattern, or ordered clusters. Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly, for example, in a Cartesian grid pattern, which can be correlated to address information by a computer.

An address within the array may be of any suitable shape and size. In some embodiments, the nucleic acid molecules are suspended in a liquid medium and contained within square or rectangular wells on the array substrate. However, the nucleic acid molecules may be contained in regions that are essentially triangular, oval, circular, or irregular. The overall shape of the array itself also may vary, though in some embodiments it is substantially flat and rectangular or square in shape.

Methylation profiling arrays may vary in structure, composition, and intended functionality, and may be based on either a macroarray or a microarray format, or a combination thereof. Such arrays can include, for example, at least 10, at least 25, at least 50, at least 100, or more addresses, usually with a single type of nucleic acid molecule at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the arrays disclosed herein include glass, Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof Array substrates can be stiff and relatively inflexible, such as glass or a supported membrane, or flexible, such as a polymer membrane. One commercially available product line suitable for probe arrays described herein is the Microlite line of MICROTITER® plates available from Dynex Technologies UK (Middlesex, United Kingdom), such as the Microlite 1+ 96-well plate, or the 384 Microlite+ 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses, for example, larger addresses will usually be found on larger arrays, while smaller addresses may be found on smaller arrays. Such a correlation is not necessary, however.

The arrays herein may be described by their densities which is the number of addresses in a certain specified surface area. For macroarrays, array density may be about one address per square decimeter, such as one address in a 10 cm by 10 cm region of the array substrate to about 50 addresses per square centimeter. For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid molecule within the sample may be labeled, such as with a fluorescent label and, after hybridization, the hybridization signals may be detected and analyzed.

Synthesis of Oligonucleotides

In vitro methods for the synthesis of oligonucleotides are well known to those of ordinary skill in the art; such methods can be used to produce primers and probes for use in the disclosed methods. Such methods can range from standard enzymatic digestion followed by nucleotide fragment isolation (see for example, Sambrook et al., *Molecular Cloning: A Laboratory Manual, 2nd Edition* (Cold Spring Harbor Laboratory Press, Cold Spring Harbor, N.Y., 1989) Chapters 5, 6) to purely synthetic methods, for example, by the cyanoethyl phosphoramidite method. The most common method for in vitro oligonucleotide synthesis is the phosphoramidite method, formulated by Letsinger and further developed by Caruthers (Caruthers et al., *Chemical synthesis of deoxyoligonucleotides*, in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach*, IRL Press, 1984.

In general, the synthesis reactions proceed as follows: A dimethoxytrityl or equivalent protecting group at the 5' end of the growing oligonucleotide chain is removed by acid treatment. The growing chain is anchored by its 3' end to a solid support such as a silicon bead. The newly liberated 5' end of the oligonucleotide chain is coupled to the 3'-phosphoramidite derivative of the next deoxynucleotide to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for example, U.S. Pat. Nos. 4,415,732, 4,458,066, 4,500,707, 4,973,679, and 5,132,418. Oligonucleotide synthesizers that employ this or similar methods are available commercially (for example, the PolyPlex oligonucleotide synthesizer from Gene Machines, San Carlos, Calif.). In addition, many companies will perform such synthesis (for example, Sigma-Genosys, The Woodlands, Tex.; QIAGEN® Operon, Alameda, Calif.; Integrated DNA Technologies, Coralville, Iowa; and TriLink Bio-Technologies, San Diego, Calif.).

The nucleotide sequence of an oligonucleotide is generally determined by the sequential order in which subunits of subunit blocks are added to the oligonucleotide chain during synthesis. Each round of addition can involve a different, specific nucleotide precursor or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction. Random hexamer oligonucleotides can be synthesized using standard β-cyanoethyl phosphoramidite coupling chemistry on mixed dA+dC+dG+dT synthesis columns such as those available from Glen Research, Sterling, Va. The four phosphoramidites typically are mixed in equal proportions to randomize the bases at each position in the oligonucleotide.

EXAMPLES

Example 1

Amplification of Bisulfite Treated DNA

This example describes the methods of amplifying DNA that retains the information about cytosine methylation status.

Figure 3:
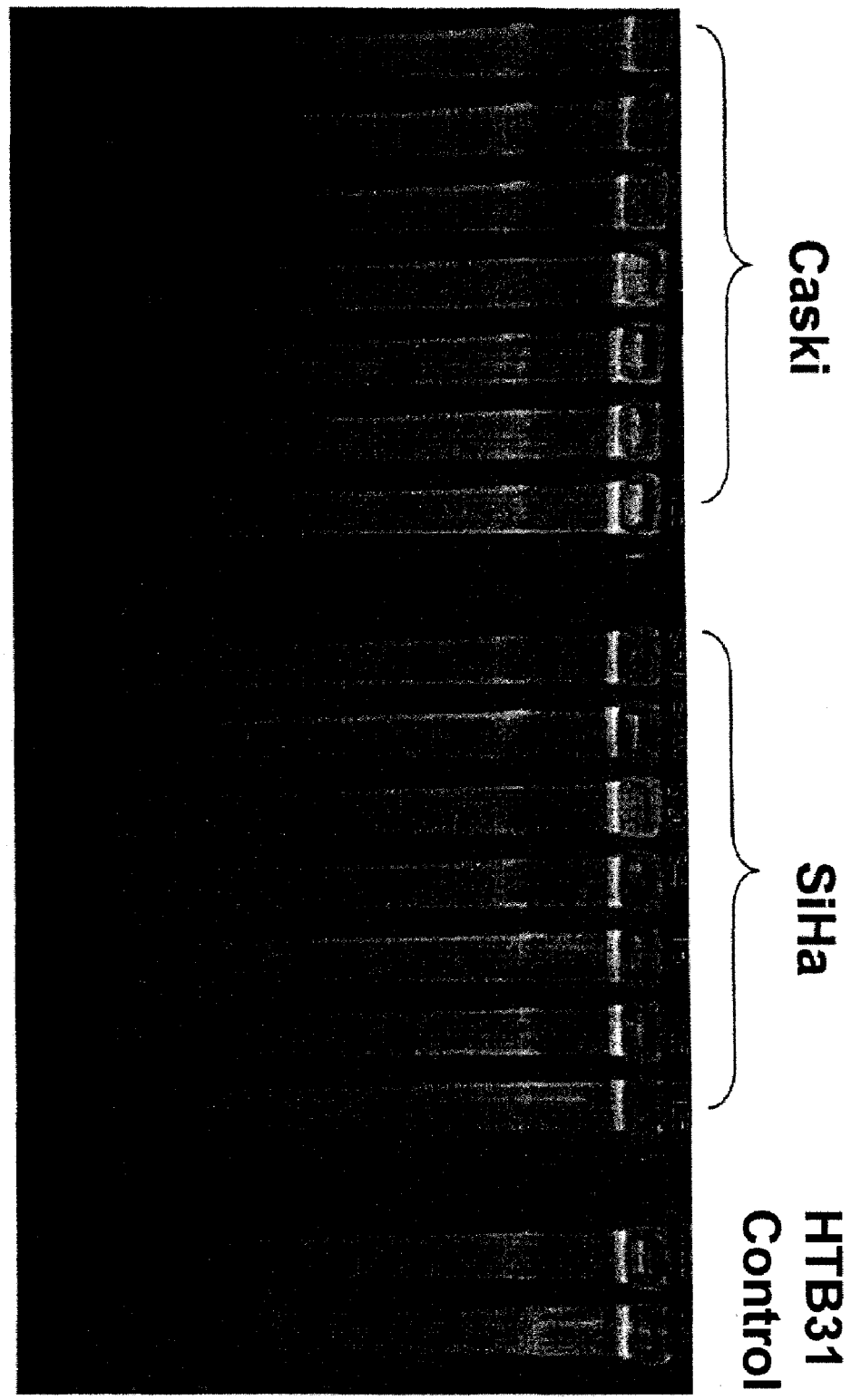
FIG. 3 is digital image of an agarose gel demonstrating that bisulfite treated DNA was amplified by multiple strand displacement.

The retention of methylation information in the Meth-DNA archive was demonstrated by quantitative comparison of methylation levels in the E6 promoter region of HPV 16 viral genome in Caski cells (derived from cervical squamous cell carcinoma, ATCC® Number: CRL-1550™). Caski cells were fixed in PRESERVCYT® (Cytyc Corporation, Boxborough, Mass.) medium and total nucleic acid (TNA) was extracted from these cells by MASTERPURE™ extraction kit (Epicentre Technologies, WI). TNA (20-500 ng) and was bisulfite treated using the EZ DNA METHYLATION KIT™ (Zymo Research, CA). The bisulfite treated DNA (BST-DNA) was recovered in 20 µl elution buffer. One microliter of BST-DNA was subjected to multiple strand displacement amplification (MDA) by φ29 DNA polymerase using the REPL1-G® whole genome amplification kit (QIAGEN®, CA) in a 50 µl reaction. This reaction with φ29 DNA polymerase on BST-DNA creates a DNA archive that preserves the information about the cytosine methylation state (Meth-DNA). During the MDA reaction, the base uracil in the BST-DNA is substituted with thymine in the Meth-DNA archives FIG. 3 shows an agarose gel demonstrating that BST-DNA was amplified by multiple strand displacement amplification.

Example 2

Analysis of Meth-DNA Archive

This example describes the comparison DNA yield from the Meth-DNA Archive and the BST-DNA that was not amplified.

Figure 4:
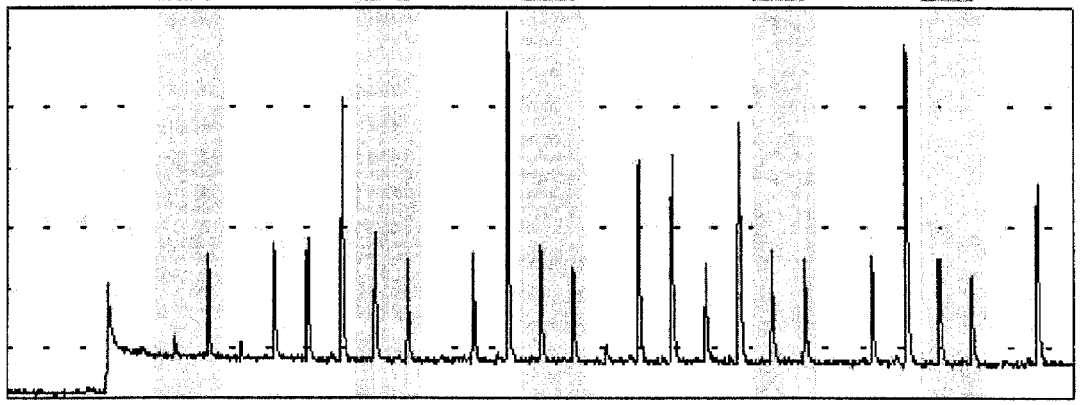
FIG. 4 is a set of representative pyrograms obtained with unamplified BST-DNA and MDA amplified BST-DNA, both at input level of 100 nanograms of Caski total nucleic acid for bisulfite treatment.
Figure 4:
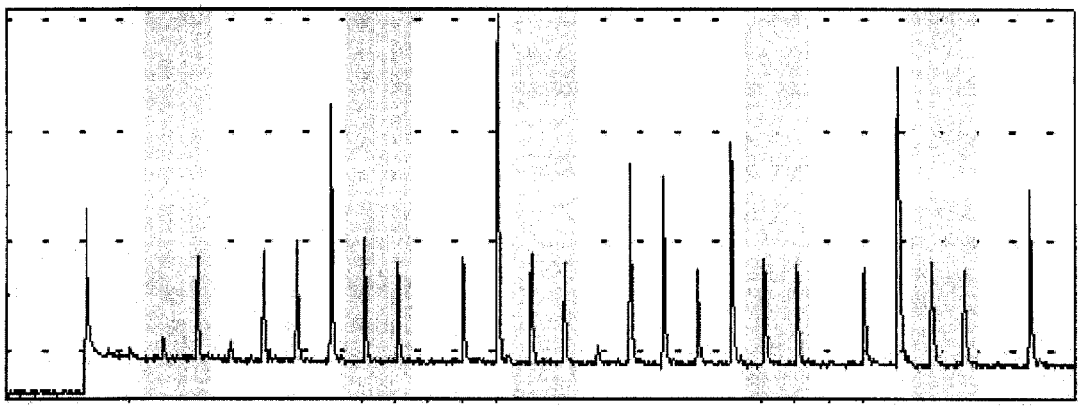
Figure 5:
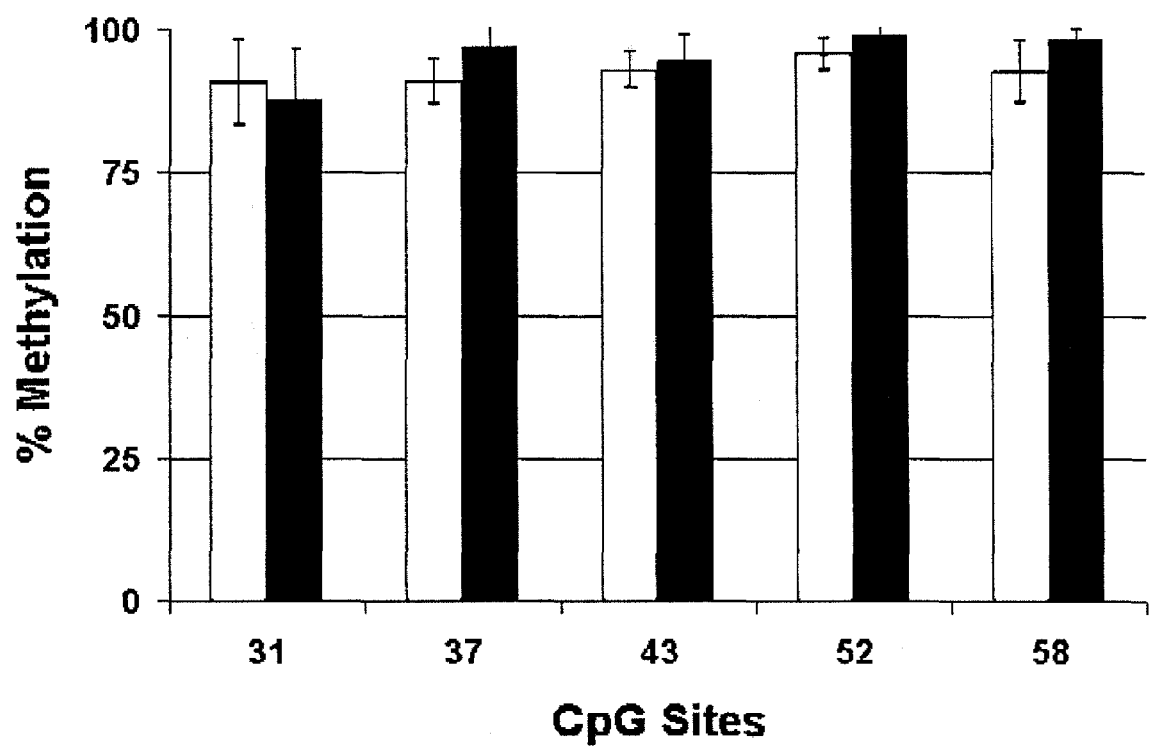
FIG. 5 is a bar graph showing the preservation of DNA methylation signatures in globally amplified DNA as reflected by mean (±SD) methylation values (%) obtained at the indicated CpG sites.

DNA from Caski Meth-DNA archive and original BST-DNA (1 µl each) were used in separate PCR (50 µl) applifications. The base uracil in the BST-DNA was substituted by thymine in PCR. Primers for PCR were designed using the sense strand of the BST-DNA and targeted 192 bp E6 promoter region covering CpG sites at nucleotide positions 31, 37, 43, 52 and 58 of HPV 16 genome. PCR product (25 µl) was subsequently used to quantify the methylation status at the above CpG sites by PYROSEQUENCING®. Because of the bisulfite conversion of base unmethylated C to T, methylation status by sequencing is detected as a C/T polymorphism. PYROSEQUENCING® enables quantitative measurement of methylation by detecting the presence of a C/T polymorphism. PYROSEQUENCING® was done using the protocols provided by Biotage, VA. Each CpG site tested in the HPV 16 E6 promoter was methylated 84-100% of the time, as determined by the original unamplified BST-DNA. The same level of methylation (83-100%) was also determined for these targets by corresponding sample from the globally amplified Meth-DNA archived, indicating excellent fidelity of the disclosed method for preserving the methylation signature in the Meth-DNA (FIG. 4). FIG. 4 shows pyrograms obtained with unamplified BST-DNA and MDA amplified BST-DNA both at an input level of 100 ng of Caski TNA for bisulfite treatment. FIG. 5 shows the preservation of DNA methylation signatures in globally amplified DNA as reflected by mean (±SD) methylation values (%) obtained with 500 ng, 100 ng and 20 ng input levels of TNA for bisulfite treatment. The original BST-DNA was determined to be amplified by 50-fold in terms of the number of PCR reactions that can be conducted with globally amplified BST-DNA by MDA.

Example 3

Archive of Cervical Tissue Obtained from Subjects

This example describes the cervical samples obtained from subjects and their storage in a tissue biorepository.

Pap smear and biopsy diagnoses as well as results of colposcopy and physical exams are being collected. Based on a pilot chart review of 150 subjects, a Microsoft Access Database to organize this information was developed. Follow-up data will be used to refine cervical disease classification at enrollment, and to identify women with persistent or recurrent disease that may correlate with greater risk for disease progression.

Significant cervical disease (CIN II and greater) was diagnosed in 20% of subjects. The "other" group includes subjects with vaginal or vulvar disease that could confuse interpretation of markers. The indeterminate category includes subjects with discordant findings as well as those with abnormal cytology that were not biopsied. The achieved cervical samples are then analyzed to determine the methylation pattern using the disclosed methods.

Example 4

Detection of HPV DNA Methylation Using PYROSEQUENCING® of Non-Amplified DNA The vast majority of HPV 16 DNA present in exfoliated cervical samples is transcriptionally silent. The ratio of HPV 16 E6/E7 transcript copies to HPV 16 DNA copies was less than 1 in 10 in clinical samples. This ratio was 0.11 for Caski (~400 HPV 16 copies/cell) and 12.23 for SiHa (1 copy of HPV 16/cell) cell lines. Methylation has been implicated in this silencing. The methylation pattern and/or methylated viral load (fraction of viral load that is subject to regulation by methylation) may affect HPV persistence and regression or progression of neoplasia. Because of this link, HPV methylation changes may serve as a biomarker for CIN 3.

Based on data from the few studies of HPV methylation to date, and the known function of the HPV genome, attention is focused on the LCR/E6 region because this region of the HPV genome harbors the p97 promoter for the E6/E7 oncogene expression, is rich in binding sites for various cellular transcription factors (AP1, NF1, Sp1, progesterone receptor, CDP, YY1), and binding sites for viral proteins E2 (4 E2 binding sites called E2Bs1-4) and E1. Using samples from the biorepository all the potential CpG methylations in the LCR/E6 region are examined and correlated with disease status.

PYROSEQUENCING® can be used to quantitatively evaluate the methylation pattern of HPV 16 DNA and assays for a limited number of potential CpG methylation (mCpG) sites in the LCR/E6-E7 region in Caski and SiHA cell lines have been developed. There are a total of 21 potential mCpG sites in the LCR/E6-E7 region from nt 6999 to 124. Of these, 10 (nt 7032, 7091, 7136, 7145, 7233, 7270, 7428, 7434, 7455, 7461,) are of unknown significance (3' of L1 and 5' of LCR regions), 5 (nt 7535, 7553, 7676, 7682, 7694) are in the enhancer region, and 6 (nt 7862, 31, 37, 43, 52, 58,) are in the E6/E7 promoter region. Seven amplicons (A-G) and 9 sequencing primers were designed to target all the 21 CpG sites in cell lines Caski and SiHa.

Based on studies of SiHa DNA, the amount of DNA for PYROSEQUENCING® has been reduced. Successful pyrosequencing was obtained with bisulfite treatment of as little as 20 ng of DNA. However results in clinical materials typically require amplification of the bisulfite treated DNA. Using bisulfite treatment of MAGNAPURE® DNA extracts from nine HPV 16-positive cervical swab samples, amplicon A from 6 and amplicon B was generated from 4 of the 9 samples tested. In addition, the C/T base assignment was successful for the CpG sites (31, 37, 43, 52, 58) in amplicon A in only 2 of the 9 samples tested.

Example 5

Amplification of Methylated DNA Obtained from a Subject

The example describes the amplification of archived DNA obtained from cervical specimens.

Samples obtained from subjects are fixed in PRESERV-CYT® (Cytyc Corporation, Boxborough, Mass.) medium and total nucleic acid (TNA) is extracted from these cells by MASTERPURE™ extraction kit (Epicentre Technologies, WI). TNA (20-500 ng) is bisulfite treated using the EZ DNA METHYLATION KIT™ (Zymo Research, CA). Bisulfite treated DNA (BST-DNA) is recovered in 20 µl elution buffer. One microliter of BST-DNA is subjected to multiple strand displacement amplification (MDA) by $\phi$29 DNA polymerase using the REPL1-G® whole genome amplification kit (QIAGEN®, CA) in a 50 µl reaction. Amplified bisulfite treated DNA is used immediately or stored for later use.

Example 6

Amplification of Methylated Blood DNA Obtained from a Subject

The example describes the amplification of DNA obtained from blood specimens.

DNA was extracted (QIAAMP® DNA Blood Mini Kit, QIAGEN®, CA) from peripheral blood mononuclear cells following the manufacturer's recommendations. 100 ng of DNA was bisulfite treated (EZ DNA METHYLATION KIT™) and recovered in 20 µl volume. One microliter of BST-DNA is subjected to multiple strand displacement amplification (MDA) by $\phi$29 DNA polymerase using the REPL1-G® whole genome amplification kit (QIAGEN®, CA) in a 50 µl reaction (average yield was 28.08 µg). Fidelity of multiple strand displacement amplification was determined by comparing a portion of unamplified DNA (25 ng for PCR) and amplified DNA (100 ng for PCR) by PYROSEQUENCING® using primers for p16 gene. The p16 PYROSEQUENCING assay determined the methylation status of 2 CpG sites in the PCR product. For three subjects, the mean methylation level for the 6 CpG sites was 4.86% and this was comparable to the mean methylation level with Meth-archive DNA (6.78%). Amplified bisulfite treated DNA is used immediately or stored for later use to detect methylation status of a number of human genes.

Example 7

Analysis of Methylation Status of Amplified DNA Obtained from a Tumor Using Microarray Analysis This example describes exemplary procedures for the analysis of amplified DNA using a nucleic acid microarray.

Bisulfite treated DNA is amplified using MDA to maintain the information about methylation status. The amplified DNA is then PCR-amplified labeled with random priming.

Oligonucleotides are designed to include two to four CpG sites of the CpG island to be interrogated. These oligonucleotides are specific to the bisulfite-converted sequence of a portion of the CpG island. Each is synthesized with an amino-linked C6 [$NH_2$ $(CH_2)_6$] linker attached to its 5' end. The oligonucleotides are suspended in 1× microspotting solution to a final concentration of 50 pmole/µL. Approximately 1 nL (0.05-0.1 pmole) of each oligonucleotide is printed in quadruplicate as microdots (100 µm diameter) on the superaldehyde-coated glass slides using a microarrayer. The slides are washed thoroughly to remove unbound oligonucleotides. For target labeling, PCR products of bisulfite-treated MDA amplified DNA are labeled at the 3' terminus with Cy5-dCTP by terminal transferase. The unincorporated dCTP is removed by passing the labeled target through a micro-Bio-spin column. The labeled product (2 µL per $cm^2$ of glass slides with ~4 pmole/µL of Cy5 incorporation) is resuspended, denatured at 95° C. for 5 min, and is applied to a glass slide. The hybridization is conducted in a moist hybridization chamber under a cover slip. The slide is rinsed and washed twice at room temperature with 2×SSC-0.2% SDS for a total of 15 min, followed by washing twice with 2×SSC at room temperature for 5 min, and is dried by centrifugation at 500 rpm for 5 min. The microarray slide is scanned and the scanned image is analyzed.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. A method for preserving information about global genomic cytosine methylation status in an amplified genome, comprising:
  contacting a genomic sample with a modifying agent comprising bisulfite that converts unmethylated cytosine residues but not methylated cytosine residues to produce a converted genomic sample, wherein the converted cytosine residues present in the converted genomic sample are distinguishable from the methylated cytosine residues to provide the information about global genomic cytosine methylation status; and
  contacting the converted genomic sample with a DNA polymerase to amplify the converted genomic sample by multiple strand displacement amplification under isothermal conditions, thereby producing an amplified genome, wherein the converted genomic sample is not contacted with a nucleic acid ligase or an RNA polymerase, thereby preserving information about global genomic cytosine methylation status in the amplified genome.

2. The method of claim 1, wherein the DNA polymerase is φ29 DNA polymerase.

3. The method of claim 1, further comprising contacting the converted genomic sample with primers capable of hybridizing under very high stringency conditions to genomic DNA in the converted genomic sample.

4. The method of claim 3, wherein the primers are six nucleotides long.

5. The method of claim 3, wherein the primers are of random nucleotide composition.

6. The method of claim 3, wherein the primers are DNA nuclease resistant.

7. The method of claim 1, further comprising contacting the genomic sample with an RNAse, thereby producing RNA fragments.

8. The method of claim 7, wherein the RNA fragments are capable of hybridizing under very high stringency conditions to the converted genomic sample.

9. The method of claim 1, wherein the modifying agent converts unmethylated cytosine residues to produce uracil.

10. The method of claim 1, wherein the genomic sample is a biological sample obtained from a subject.

11. A method for preserving information about global genomic cytosine methylation status in an amplified genome, consisting of:
   contacting a genomic sample with a modifying agent comprising bisulfite that converts unmethylated cytosine residues but not methylated cytosine residues to produce a converted genomic sample, wherein the converted cytosine residues present in the converted genomic sample are distinguishable from the methylated cytosine residues to provide the information about global genomic cytosine methylation status;
   contacting the converted genomic sample with primers capable of hybridizing under very high stringency conditions to genomic DNA in the converted genomic sample; and
   contacting the converted genomic sample with a DNA polymerase to amplify the converted genomic sample by multiple strand displacement amplification under isothermal conditions, thereby producing an amplified genome, wherein the converted genomic sample is not contacted with a nucleic acid ligase or an RNA polymerase, thereby preserving information about global genomic cytosine methylation status in the amplified genome.

12. The method of claim 11, wherein the DNA polymerase is φ29 DNA polymerase.

13. The method of claim 11, wherein the primers are six nucleotides long.

14. The method of claim 11, wherein the primers are of random nucleotide composition.

15. The method of claim 11, wherein the primers are DNA nuclease resistant.

16. The method of claim 11 wherein the modifying agent converts unmethylated cytosine residues to produce uracil.

17. The method of claim 11, wherein the genomic sample is a biological sample obtained from a subject.

18. A method for detecting cytosine methylation in a genomic sample wherein information about global genomic cytosine methylation has been preserved, the method comprising:
   contacting a genomic sample with a modifying agent comprising bisulfite that converts unmethylated cytosine residues but not methylated cytosine residues in the genomic sample to produce a converted genomic sample, wherein the converted cytosine residues present in the converted genomic sample are distinguishable from the methylated cytosine residues to provide the information about global genomic cytosine methylation status;
   contacting the converted genomic sample with primers capable of hybridizing under very high stringency conditions to genomic DNA in the converted genomic sample; and
   contacting the converted genomic sample with a DNA polymerase to amplify the converted genomic sample by multiple strand displacement amplification under isothermal conditions, thereby producing an amplified genome, wherein the converted genomic sample is not contacted with a nucleic acid ligase or an RNA polymerase, thereby preserving information about global genomic cytosine methylation status in the amplified genome; and detecting methylated cytosine in the sample, wherein detecting methylated cytosine comprises:
   determining a nucleic acid sequence of a portion of the amplified genome; and
   comparing the sequence of the portion of the amplified genome to a control, wherein a difference between the sequence of the portion of the amplified genome and the control detects methylated cytosine in the genomic sample.

19. The method of claim 18, wherein the control is a known DNA sequence corresponding to the nucleic acid sequence of a portion of the amplified genome.

20. The method of claim 18, wherein the control is a DNA sequence of a nucleic acid molecule that has not been contacted with the modifying agent and corresponds to the sequence of the portion of the amplified genome.

21. The method of claim 18, wherein determining a nucleic acid sequence of a portion of the amplified genome comprises DNA sequencing, polymerase chain reaction (PCR), nucleic acid hybridization, endonuclease digestion, or a combination thereof.

22. The method of claim 21, wherein DNA sequencing comprises pyrosequencing.

23. The method of claim 21, wherein nucleic acid hybridization comprises the use of a microarray.

24. The method of claim 18, wherein the DNA polymerase is φ29 DNA polymerase.

25. The method of claim 18, wherein the primers are six nucleotides long.

26. The method of claim 18, wherein the primers are of random nucleotide composition.

27. The method of claim 18, wherein the primers are DNA nuclease resistant.

28. The method of claim 18, wherein the genomic sample is a biological sample obtained from a subject.

29. The method of claim 3, wherein the primers are DNA nuclease resistant random hexamers.

30. The method of claim 11, wherein the primers are DNA nuclease resistant random hexamers.

31. The method of claim 18, wherein the primers are DNA nuclease resistant random hexamers.

32. The method of claim 1, wherein preserving information about global genomic cytosine methylation status comprises creating an archive of methylated DNA.

* * * * *